(12) United States Patent
Wennerbäck et al.

(10) Patent No.: US 8,741,083 B2
(45) Date of Patent: Jun. 3, 2014

(54) ELASTIC LAMINATE AND A METHOD FOR PRODUCING AN ELASTIC LAMINATE

(75) Inventors: Margareta Wennerbäck, Mölnlycke (SE); Jan Wästlund-Karlsson, Mölndal (SE); Elisabeth Lakso, Stenungsund (SE)

(73) Assignee: SCA Hygiene Products AB, Göteborg (SE)

( * ) Notice: Subject to any disclaimer, the term of this patent is extended or adjusted under 35 U.S.C. 154(b) by 431 days.

(21) Appl. No.: 12/300,398

(22) PCT Filed: May 12, 2006

(86) PCT No.: PCT/SE2006/000564
§ 371 (c)(1),
(2), (4) Date: Nov. 11, 2008

(87) PCT Pub. No.: WO2007/133128
PCT Pub. Date: Nov. 22, 2007

(65) Prior Publication Data
US 2009/0208703 A1    Aug. 20, 2009

(51) Int. Cl.
| | | |
|---|---|---|
| *B32B 3/10* | (2006.01) |
| *B32B 3/24* | (2006.01) |
| *B32B 5/04* | (2006.01) |
| *B32B 5/26* | (2006.01) |
| *B32B 37/02* | (2006.01) |
| *B32B 37/12* | (2006.01) |
| *B32B 37/15* | (2006.01) |
| *B32B 37/16* | (2006.01) |
| *B32B 38/00* | (2006.01) |
| *B32B 38/04* | (2006.01) |
| *B32B 3/28* | (2006.01) |
| *B32B 27/12* | (2006.01) |
| *B32B 37/20* | (2006.01) |

(52) U.S. Cl.
USPC .......... 156/163; 156/160; 156/164; 156/210; 156/229; 156/244.11; 156/250; 156/252; 156/256; 156/290; 156/291; 156/292; 428/137; 428/138; 428/182; 428/189; 428/190; 428/340; 442/381; 442/382; 442/392; 442/394; 442/399; 442/400; 442/401

(58) Field of Classification Search
None
See application file for complete search history.

(56) References Cited

U.S. PATENT DOCUMENTS 4,655,760 A * 4/1987 Morman et al. .......... 604/385.26
4,692,368 A * 9/1987 Taylor et al. .................. 428/137

(Continued)

FOREIGN PATENT DOCUMENTS

EP    0 650 714 A1    5/1995
EP    0 714 351 B1    6/1996

(Continued)

OTHER PUBLICATIONS

PTO/ISA/210.

(Continued)

*Primary Examiner* — Aaron Austin
*Assistant Examiner* — Jeff Vonch
(74) *Attorney, Agent, or Firm* — Buchanan Ingersoll & Rooney PC

(57) ABSTRACT

A method for producing an elastically stretchable laminate having at least three layers, the method including the steps of: a) producing a first laminate having a first non-elastic fibrous nonwoven web and an elastic film; b) activating the first laminate by incremental stretching in at least one activation direction to render the first laminate elastically stretchable; c) stretching the activated first laminate to 10-200% in the activation direction; and d) laminating the stretched first laminate to a second non-elastic nonwoven web. An elastically stretchable laminate produced in accordance with the method is also disclosed.

20 Claims, 3 Drawing Sheets

(56) References Cited

U.S. PATENT DOCUMENTS

| | | |
|---|---|---|
| 4,704,115 A | 11/1987 | Buell |
| 4,771,483 A * | 9/1988 | Hooreman et al. ............... 2/237 |
| 4,842,596 A | 6/1989 | Kielpikowski et al. |
| 5,143,679 A | 9/1992 | Weber et al. |
| 5,156,793 A | 10/1992 | Buell et al. |
| 5,167,897 A | 12/1992 | Weber et al. |
| 5,342,343 A * | 8/1994 | Kitaoka et al. ............ 604/385.29 |
| 5,422,172 A | 6/1995 | Wu |
| 5,576,090 A * | 11/1996 | Suzuki ......................... 428/152 |
| 5,592,690 A | 1/1997 | Wu |
| 5,634,216 A | 6/1997 | Wu |
| 5,711,832 A | 1/1998 | Glaug et al. |
| 5,733,628 A | 3/1998 | Pelkie |
| 5,855,574 A * | 1/1999 | Kling et al. .................. 604/392 |
| 5,855,999 A | 1/1999 | McCormack |
| 5,861,074 A | 1/1999 | Wu |
| 5,939,178 A * | 8/1999 | Boich .......................... 428/198 |
| 5,964,973 A * | 10/1999 | Heath et al. .................... 156/161 |
| 5,997,981 A | 12/1999 | McCormack et al. |
| 6,054,727 A | 4/2000 | Voss |
| 6,149,637 A | 11/2000 | Allen et al. |
| 6,313,372 B1 * | 11/2001 | Suzuki .......................... 604/365 |
| 6,506,698 B1 | 1/2003 | Quantrille et al. |
| 6,673,980 B1 | 1/2004 | Mace et al. |
| 6,911,106 B2 | 6/2005 | Varona et al. |
| 7,008,496 B2 | 3/2006 | Morman |
| 2002/0002021 A1 | 1/2002 | May et al. |
| 2003/0024625 A1 | 2/2003 | McAmish et al. |
| 2003/0105446 A1 * | 6/2003 | Hutson et al. ............ 604/385.22 |
| 2004/0040642 A1 * | 3/2004 | Otsubo et al. ................. 156/163 |
| 2004/0102754 A1 * | 5/2004 | Morman et al. ......... 604/385.24 |
| 2004/0108043 A1 | 6/2004 | Otsubo |
| 2004/0112509 A1 * | 6/2004 | Morman ....................... 156/163 |
| 2004/0127528 A1 | 7/2004 | Eriksson et al. |
| 2004/0133180 A1 | 7/2004 | Mori et al. |
| 2004/0158217 A1 * | 8/2004 | Wu et al. .................. 604/385.01 |
| 2004/0192140 A1 * | 9/2004 | Schneider et al. ............ 442/329 |
| 2004/0241389 A1 | 12/2004 | Chung et al. |
| 2004/0243089 A1 | 12/2004 | Veith et al. |
| 2005/0101216 A1 | 5/2005 | Middlesworth et al. |
| 2005/0126689 A1 | 6/2005 | Thorson et al. |
| 2005/0136778 A1 | 6/2005 | Thomaschefsky et al. |
| 2005/0230037 A1 * | 10/2005 | Jenquin et al. ................ 156/256 |
| 2005/0257881 A1 * | 11/2005 | Coose et al. .................. 156/256 |
| 2006/0083900 A1 * | 4/2006 | Ashraf .......................... 428/182 |
| 2006/0144503 A1 * | 7/2006 | Carr .............................. 156/164 |
| 2006/0148358 A1 * | 7/2006 | Hall et al. ..................... 442/328 |
| 2006/0148361 A1 | 7/2006 | Ng et al. |
| 2006/0254708 A1 | 11/2006 | Wada et al. |
| 2008/0009817 A1 | 1/2008 | Norrby |
| 2009/0038751 A1 | 2/2009 | Hermansson et al. |
| 2013/0240123 A1 | 9/2013 | Lakso et al. |

FOREIGN PATENT DOCUMENTS

| | | | |
|---|---|---|---|
| EP | 0 715 351 B1 | 6/1996 | |
| EP | 1 688 113 A1 | 8/2006 | |
| JP | H05-245961 A | 9/1993 | |
| JP | H06-047808 A | 2/1994 | |
| JP | 8-280741 A | 10/1996 | |
| JP | H09-078431 A | 3/1997 | |
| JP | H09-503167 A | 3/1997 | |
| JP | H09-504488 A | 5/1997 | |
| JP | 2003-025471 A | 1/2003 | |
| JP | 2004-305771 A | 11/2004 | |
| JP | 2005-511345 A | 4/2005 | |
| JP | 2005-178365 A | 7/2005 | |
| JP | 2008-503315 A | 2/2008 | |
| JP | 2008-514269 A | 5/2008 | |
| RU | 2140855 C1 | 11/1999 | |
| RU | 2205757 C2 | 6/2003 | |
| RU | 2283238 C2 | 9/2006 | |
| RU | 2006122606 A | 1/2008 | |
| WO | WO 95/04654 A1 | 2/1995 | |
| WO | WO 95/18589 A1 | 7/1995 | |
| WO | WO 00/45764 A1 | 8/2000 | |
| WO | WO 03/047488 A1 | 6/2003 | |
| WO | WO 03/070140 A1 | 8/2003 | |
| WO | WO 2004/078083 A1 | 9/2004 | |
| WO | WO 2005/122985 A1 | 12/2005 | |
| WO | WO 2006/007200 A2 | 1/2006 | |
| WO | WO 2006/036090 A1 | 4/2006 | |
| WO | WO 2006/093440 A1 | 9/2006 | |
| WO | WO 2008/060204 A1 | 5/2008 | |
| WO | WO 2008/060205 A1 | 5/2008 | |

OTHER PUBLICATIONS

PCT/ISA/237.
PCT/IPEA/409.
Lakso et al, Copending U.S. Appl. No. 12/300,413, filed Nov. 11, 2008, entitled "A Pant-Type Absorbent Article and a Method for Producing Pant-Type Absorbent Articles".
Lakso et al., Copending U.S. Appl. No. 12/300,357, filed Nov. 11, 2008, entitled "Pant-Type Absorbent Article and a Method for Producing Pant-Type Absorbent Articles".
Official Decision of Grant dated Jun. 1, 2010 issued in corresponding RU patent application No. 2008148969, and English-language translation thereof.
Official Action of Oct. 26, 2012, issued in U.S. Appl. No. 12/300,413, 17 pages, U.S. Patent and Trademark Office.
Official Action of Jul. 1, 2011, issued in U.S. Appl. No. 12/300,413, 23 pages, U.S. Patent and Trademark Office.
Official Action of Aug. 30, 2012 issued in U.S. Appl. No. 12/300,357, 19 pages, U.S. Patent and Trademark Office.
Official Action of Mar. 27, 2012 issued in U.S. Appl. No. 12/300,357, 18 pages, U.S. Patent and Trademark Office.
English-language translation of Office Action in Japanese Patent Application No. 2009-510919, mailed Jan. 17, 2012, 3 pages, Japan Patent Office, JP.
English-language translation of Office Action in Japanese Patent Application No. 2009-509475, mailed Jun. 28, 2011, 3 pages, Japan Patent Office, JP.
Official Decision of Grant dated Jun. 1, 2010 issued in corresponding RU Patent Application No. 2008148969 (2 pages), and English-language translation thereof (4 pages), Russian Patent Office, RU.
Supplemental European Search Report in European Patent Application No. 06733408.6, May 17, 2011, seven pages, EPO, Munich, DE.
Notice of Reasons for Rejection mailed Apr. 26, 2011 in corresponding Japanese Patent Application No. 2009-510913, Japan Patent Office, JP (1 page), and English-language translation thereof (5 pages).
Supplementary European Search Report issued on Aug. 19, 2011 by the European Patent Office in corresponding European Patent Application No. 06 74 7782.

* cited by examiner

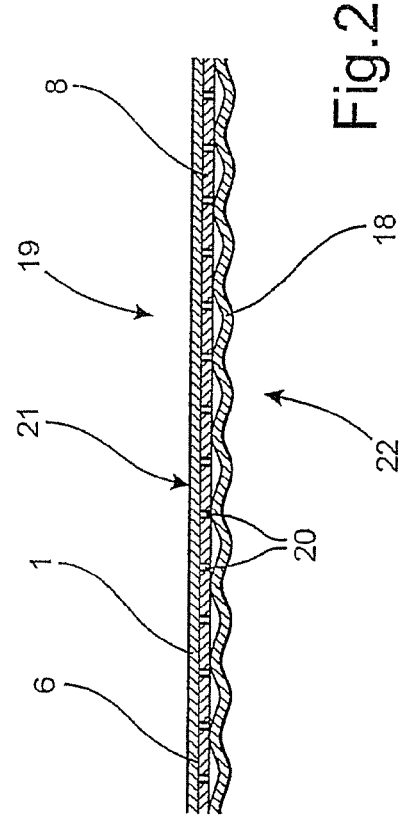
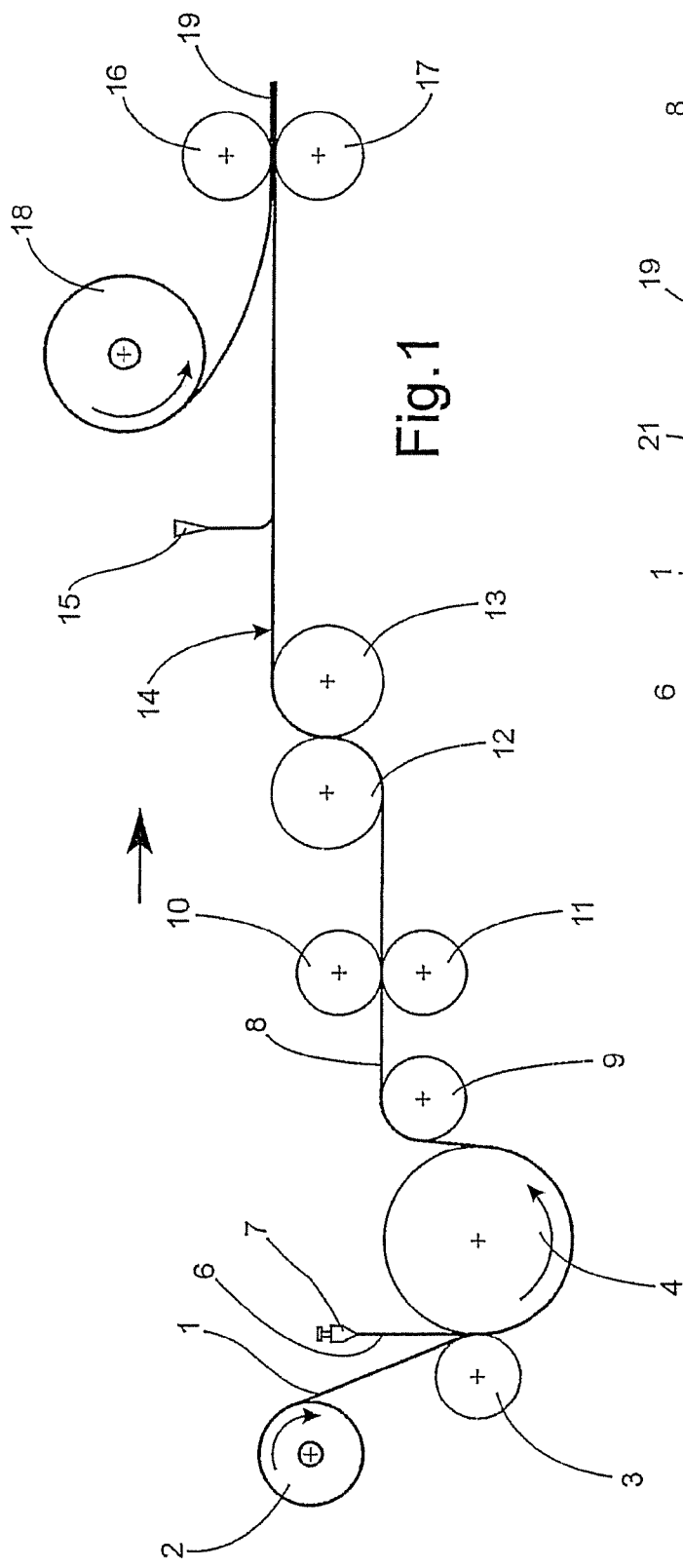

ELASTIC LAMINATE AND A METHOD FOR PRODUCING AN ELASTIC LAMINATE

PRIORITY

The present application is a national stage application of PCT/SE2006/000564, filed 12 May 2006.

TECHNICAL FIELD

The disclosure pertains to a method for producing an elastic laminate comprising at least three layers. The disclosure also concerns an elastically stretchable laminate comprising a first non-elastic nonwoven web, a second non-elastic nonwoven web and an elastic perforated film between the first and the second nonwoven webs. The elastic laminates according to the disclosure are particularly suitable for use in disposable pant articles such as pant diapers, sanitary pants, incontinence pants, and the like. Such articles comprise an absorbent unit arranged in a pant-shaped chassis and are worn in the manner of a pair of underpants.

BACKGROUND ART

Pant-type absorbent articles include a pant-shaped chassis structure and an integrated absorbent core component. The aim when constructing pant articles is to make them resemble ordinary underwear as closely as possible. Hence, absorbent articles such as pant diapers, sanitary pants and incontinence pants are designed to fit comfortably and snugly about the wearer. It is desirable that the articles are capable of being pulled up and down over the hips of the wearer to allow the wearer or caregiver to easily remove a soiled article and replace it with a new clean article. For these reasons, the article chassis is usually made of a material that is elastically stretchable, at least in the areas intended to be applied over the wearer's hips. Furthermore, it is desirable that the chassis surrounding the absorbent parts of the pant article is permeable to air and vapour, i.e. that it is breathable. A breathable article prevents moisture from remaining on the skin of the wearer and is more comfortable and less warm to wear than a non-breathable article. It is also beneficial if the article is soft, smooth and textile-like, so that it does not chafe the skin of the wearer and so that it resembles ordinary underwear as closely as possible.

Moreover, it is desirable that the absorbent pant article can be pulled up over the hips of a wearer without rupturing. A common problem is that the wearer or the caregiver ruins the pant by inadvertently running the fingers through the material when trying to get a good grip for pulling up or removing the pant.

A previously used elastic material for pant articles is a laminate comprising an elastic film sandwiched between two layers of non-elastic nonwoven. In order to render the laminate elastically stretchable, it is subjected to an activation treatment. A three-layer, activated laminate is disclosed in International Patent Application No. WO 03/047488. The activated laminate is produced by incrementally stretching an elastic film layer between two non-elastic cloth-like layers. Incremental stretching is carried out by passing the laminate between intermeshing gear rollers. Activation of elastic laminates by incremental stretching is also disclosed in U.S. Pat. Nos. 5,143,679, 5,156,793 5,167,897, 5,422,172, 5,592,690, 5,634,216 and 5,861,074. The non-elastic cloth-like layers are fully or partially broken or torn during the activation process so that the elasticity of the laminate after activation is mainly governed by the elasticity of the elastic film layer. In the three-layer laminate in WO 03/047488, the non-elastic layers are completely broken so that the elasticity of the activated laminate is substantially the same as the elasticity of the elastic film layer.

The disclosed laminates have excellent comfort properties and are soft, breathable and elastic. However, a major disadvantage with the known laminates is that the activation process at least partially breaks and destroys the cloth-like layers resulting in an activated laminate having decreased tensile strength and puncture resistance. When used as a chassis component in a disposable pant article, the material is easily torn when exposed to the forces arising when putting on or pulling off the pant article. This tearing problem is particularly pronounced for female wearers or caregivers who often have long fingernails that may penetrate and tear the pant material.

Hence, there exists a need for an improved elastically stretchable, textile-like laminate for use in disposable pant articles. Moreover, there exists a need for a process for producing such a laminate.

OBJECTS AND SUMMARY

Accordingly, an object of the disclosure is to provide an elastically stretchable textile-like laminate having improved tensile strength and puncture resistance. A further object of the disclosure is to provide a method for producing an elastically stretchable textile-like laminate having improved tensile strength and puncture resistance.

The disclosure provides a method for producing an elastically stretchable laminate comprising at least three layers. The method in accordance with an embodiment of the disclosure comprises the steps of:

a) producing a first laminate comprising a first non-elastic fibrous nonwoven web and an elastic film;
b) activating the first laminate by incremental stretching to render the first laminate elastically stretchable;
c) stretching the activated first laminate by 10-200% in at least one direction;
d) laminating the stretched first laminate to a second non-elastic nonwoven web.

The first laminate can be made in any suitable way, including by adhesive bonding, thermo-bonding and extrusion coating of the first nonwoven web with an elastic film-forming polymer.

The amount of stretching of the first laminate is specified as a percentage of the initial, non-stretched extension of the laminate in the direction of stretch. By way of example, a laminate having a first, non-stretched length of 1 m and being stretched by 50% has a second, stretched length of 1.5 m.

According to a preferred embodiment of the disclosure, the first laminate is produced by extrusion coating the fibrous nonwoven web with the elastic plastic film.

The elastic film is preferably perforated in order to provide breathability in the produced laminate. When bonding the first nonwoven web to the elastic film by means of extrusion coating, the perforating step can be made by passing the combined elastic layer and nonwoven web over a vacuum lamination drum while the elastic layer is in a molten or semi-molten state. Such a process is disclosed in U.S. Pat. No. 5,733,628 and results in the elastic film being formed into a three-dimensional apertured laminate layer.

The activation step involves incremental stretching of the first laminate so that the non-elastic material is broken, at least partially. Activation can be carried out by means of heated or non-heated intermeshing gear rollers having circumferentially arranged teeth that intermesh and thereby stretch the laminate. The activation step allows the laminate to be subsequently stretched without being appreciably restrained by the non-elastic nonwoven web. The degree of breaking of the non-elastic nonwoven material decides the maximum possible elongation for the resulting laminate. If the nonwoven material is completely broken in the activation process, the laminate will have substantially the same maximum elongation as the elastic film layer.

Before carrying out the second laminating step, the first laminate is stretched in at least one direction by 10-200% of its initial, non-stretched extension. By choosing and controlling the amount of stretch, it is possible to obtain a selected elasticity in the end laminate. The first laminate is preferably stretched by 35-180% of its non-stretched extension, more preferably by 50-150% of its non-stretched extension and most preferably by 70-120% of its non-stretched extension before lamination with the second non-elastic nonwoven web.

The second non-elastic nonwoven web can be adhesively bonded to the activated first laminate.

Alternatively, the second non-elastic nonwoven web can be thermally or ultrasonically bonded to the activated first laminate. Thermal or ultrasonical bonding can be in the form of discreet bonds such as spot bonds or line bonds. By selecting a bond pattern of sparsely distributed spot bonds, it is possible to achieve a higher flexibility in the resulting laminate than with a bond pattern occupying a large proportion of the interface between the bonded layers.

The materials in the laminate are preferably in the form of running webs. The webs can be of equal width to produce a three-layer laminate that can be subsequently continuously introduced in the manufacturing process for a disposable pant article and form elastic portions of the article chassis. Alternatively, the laminate can be cut and shaped into separate elements that are used to produce a disposable pant article.

Alternatively, it is possible to produce a laminate wherein the second non-elastic nonwoven web has a width greater than the width of the first laminate. Such a three-layer laminate is suitably continuously introduced in the process when producing disposable pant articles and may form both elastic and non-elastic portions of the article chassis.

Further, two or more running first laminate webs may be bonded to the second non-elastic nonwoven web. The different bi-laminate webs may have been stretched to a different extent and/or may be made of different combinations of materials.

The first and second non-elastic fibrous nonwoven webs may comprise thermoplastic fibres. Examples of suitable polymers for use in the fibrous nonwoven webs are polyethylene, polyesters, polypropylene and other polyolefin homopolymers and copolymers. A particularly well suited nonwoven web comprises thermoplastic fibres that are a blend of polypropylene and polyethylene fibres. The preferred webs have a high content of thermoplastic fibres and contain at least 50% thermoplastic fibres and preferably at least 80% thermoplastic fibres. The second and/or non-elastic fibrous nonwoven web will typically be incorporated in joins and seams in a disposable pant article. Hence, it is highly desirable that the nonwoven webs be weldable by heat or by ultrasonic welding processes.

A suitable type of nonwoven webs for use particularly as the second non-elastic nonwoven web is a creped nonwoven. Creped nonwovens generally have greater extensibility and flexibility than non-creped nonwovens. By choosing a creped nonwoven for the second non-elastic nonwoven web, it is possible to achieve a final three-layer laminate having better properties with regard to softness and conformability than with a non-creped nonwoven. The creped nonwoven makes it easier for the three-layer laminate to contract after elongation, thus increasing the elasticity when compared to a corresponding laminate having a non-creped second nonwoven layer. If desired, the first non-elastic nonwoven web can also be a creped nonwoven.

The elastic film used for producing the three-layer laminate in accordance with the disclosure may be of any suitable elastic polymer, natural or synthetic. One example of an elastic film that has proven to provide good elasticity and breathability is an apertured three-layer elastomeric film with the composition polyethylene-styrene/ethylene/butadiene/styrene-polyethylene (PE-S EBS-PE).

In this context, an elastic material is defined as a material having a permanent elongation after relaxation of less than 10% after the material has been subjected to an elongation of 30% in the elasticity test specified in the description.

A non-elastic material is a material that does not fall within the definition of an elastic material. Accordingly, a non-elastic material as used herein is a material that may be stretchable or non-stretchable. In the case of a stretchable material, the material has a permanent elongation after stretching and relaxation of more than 10% after having been subjected to an elongation of 30% as determined according to the elasticity test.

The disclosure also provides an elastically stretchable laminate comprising a first non-elastic nonwoven web, a second non-elastic nonwoven web and an elastic perforated film between the first and the second nonwoven webs. The first non-elastic nonwoven web and the elastic perforated film form parts of a first elastic laminate that has been rendered elastic by incremental stretching and partial tearing of the nonwoven web. The first elastic laminate has then been bonded to the second nonwoven layer while in a stretched state, whereby the laminate is elastically stretchable.

Accordingly, the three-layer laminate in accordance with the disclosure comprises a first elastic bi-laminate including a nonwoven web and an elastic perforated film. The elastic bi-laminate is composed of a layer of fibrous material and an elastic layer. The fibrous layer is chosen so that it provides a soft and cloth-like feel and appearance to the laminate. Examples of suitable materials are meltblown webs and spunbond materials, and creped nonwovens, as set out above. Such materials are also suitable for the second nonwoven web that is attached to the bi-laminate. However, any soft, flexible and preferably extensible nonwoven materials and nonwoven laminates may be used, such as Spunbond-Meltblown-Spunbond-laminates (SMS), carded and spunlaced materials.

The basis weight of the first nonwoven web is suitably from 10-80 g/m$^2$ and preferably from 13-50 g/m$^2$. Examples of suitable polymers used in the fibrous material are polyethylene, polyesters, polypropylene and other polyolefin homopolymers and copolymers. Natural fibres, for example cotton, may also be used as long as they provide the desired properties. A mixture of polymers can contribute to a higher flexibility of the nonwoven layer, and through this, give the nonwoven material a higher elongation at maximum load. A mixture of polyethylene and polypropylene polymers has proven to provide good results in this respect. A mixture of fibres of different polymers is also possible.

According to one embodiment of the disclosure, the elastic layer is an apertured elastic film having a basis weight of between 10 and 120 g/m$^2$, preferably between 15 and 60 g/m$^2$. The film may be of any suitable elastic polymer, natural or synthetic. Some examples of useful materials for the elastic film are low crystallinity polyethylenes, metallocene-catalyzed low crystallinity polyethylenes, ethylene vinyl acetate copolymers (EVA), polyurethane, polyisoprene, butadiene-styrene copolymers, styrene block copolymers, such as styrene/isoprene/styrene (SIS), styrene/butadiene/styrene (SBS), or styrene/ethylene-butadiene/styrene block copolymer. Blends of these polymers may also be used as well as other modifying elastomeric or non-elastomeric materials. One example of a suitable film is an apertured three-layer elastomeric film with the composition polyethylene-styrene/ethylene/butadiene/styrene-polyethylene (PE-S EBS-PE).

The elastic bi-laminate can, for instance, be manufactured and activated according to either of the methods disclosed in WO 03/047488 or EP 0 714 351 by applying the nonwoven web to one side of the film. The nonwoven web and the film may be extrusion bonded or may be bonded by adhesive. The bi-laminate is incrementally stretched to activate the elasticity of the film layer. Incremental stretching can be made to a point below the elongation at peak load of the non-elastic nonwoven web to retain some strength in the nonwoven web. Alternatively, the stretching may be carried out so that the nonwoven is completely torn, as disclosed in WO 03/047488.

The activated bi-laminate is, according to the disclosure, further laminated to a non-elastic nonwoven web. This second lamination process is carried out while the bi-laminate is stretched in at least one direction by 10-200% of its initial, non-stretched extension, preferably by 35-180% of its non-stretched extension, more preferably by 50-150% of its non-stretched extension and most preferably by 70-120% of its non-stretched extension.

The second and/or first non-elastic nonwoven web preferably comprises a high content, i.e. at least 50% and preferably at least 80% of thermoplastic polymer fibres, such as polyethylene, polypropylene and polyester. In a preferred embodiment of the disclosure, the second and/or first non-elastic nonwoven web comprises at least 80% polypropylene fibres.

The two-step lamination process results in a three-layer laminate having a smooth face on the surface where the first nonwoven web is applied and a somewhat gathered, puckered face on the opposing surface, where the second nonwoven web is applied. When utilised as a stretchable component in a pant article, the three-layer laminate can be oriented with the smooth face on the inside of the article and the irregular face facing outwardly. In this manner, the skin-contacting parts of the laminate will be particularly soft, smooth and non-chafing against the wearer's skin. However, it is alternatively possible to arrange the laminate with the smooth face on the outside of the absorbent article. In this manner, an absorbent article having a smooth surface in contact with any clothing worn over the absorbent article is obtained. Such an embodiment can be advantageous when the article is a pair of sanitary pants or incontinent pants for adults. The smooth surface of the laminate can prevent clothing from frictionally engaging with the surface of the article and reduces the risk of riding-up and wrinkling of pants and skirts in the area overlying the pant article. Moreover, a smooth outer surface is aesthetically pleasing and will be less conspicuous when the absorbent article is worn under thin or tight-fitting garments.

The three-layer laminate in accordance with the disclosure is soft, elastic and textile-like and has considerably higher tensile strength and puncture resistance than the previously known laminates. Hence, when used in a pant article, the three-layer laminate considerably reduces the risk of unintentionally destroying the pant when pulling it up or down over a wearer's hips.

BRIEF DESCRIPTION OF DRAWINGS

The disclosure will in the following be described in greater detail with reference to exemplary embodiments shown in the appended drawings, wherein FIG. 1 shows a laminating process in accordance with an embodiment of the disclosure, FIG. 2 shows a three-layer laminate in accordance with an embodiment of the disclosure.

DETAILED DESCRIPTION OF THE PREFERRED EMBODIMENT

Figure 3:
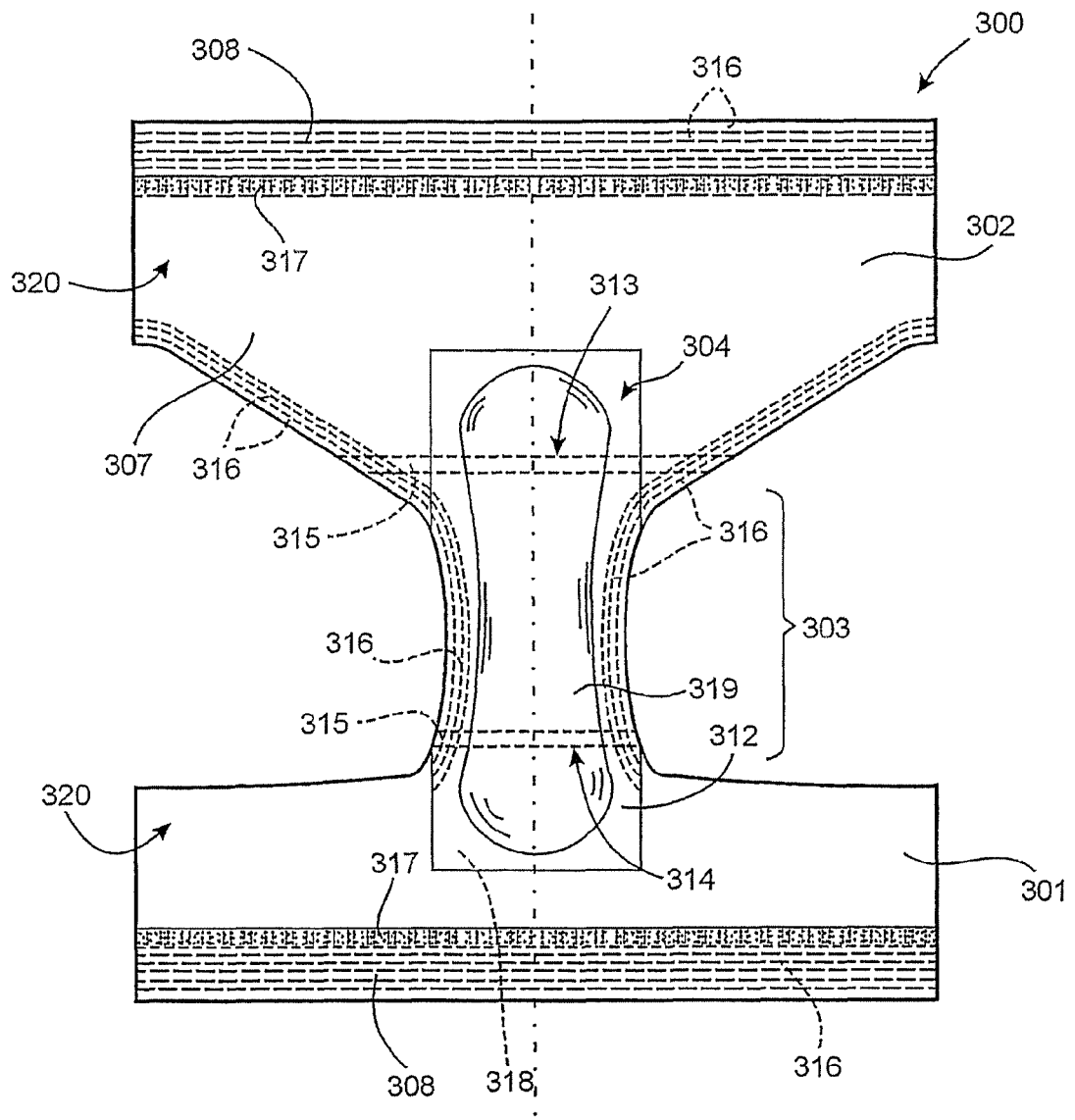
FIG. 3 shows a planar view of a pant diaper with the side joins open.

FIG. 1 shows schematically a method for producing an elastically stretchable three-layer laminate in accordance with an embodiment of the disclosure. A first non-elastic nonwoven web 1 is fed from a storage roll 2 into a first bonding nip between a rubber roll 3 and a metal roll 4. A molten elastic film-forming polymer 6 is extruded through a die 7 into the nip and the first non-elastic nonwoven web 1 and the elastic film forms a first laminate 8 that is taken off at roller 9. The first laminate 8 is subsequently activated by passing the laminate between intermeshing gear rollers 10,11 so that the first laminate 8 is subjected to incremental stretching. A number of different stretching techniques exist, as set out in EP 0 714 351. Depending on the design of the intermeshing gear rollers, the incremental stretching can be made to stretch the laminate diagonally, in the machine direction (MD) or in the cross direction (CD). The amount of breakage of the first nonwoven web caused by the incremental stretching can be controlled by adjusting the intermeshing depth of the teeth or intermeshing elements on the gear rollers. The incremental stretching releases or activates the elasticity of the elastic film and allows the two-layer first laminate 8 to be elastically extended.

In a second lamination step, the first laminate 8 is stretched by passing between a pair of rollers 12,13 driven at different speeds. The first laminate 8 is stretched in at least one direction by 10-200% of its initial, non-stretched extension. By choosing and controlling the amount of stretch, it is possible to obtain a selected elasticity in the end laminate. The first laminate 8 is preferably stretched by 35-180% of its non-stretched extension, more preferably by 50-150% of its non-stretched extension and most preferably by 70-120% of its non-stretched extension after activation before it is laminated with the second non-elastic nonwoven web 18. The degree of stretching of the first laminate 8 is a major factor in determining the elasticity of the final three-layer laminate 19. Other factors that influence the elasticity of the final three-layer laminate are the flexibility and extensibility of the second non-elastic nonwoven web 18. The bonded area between the first laminate and 8 and the second non-elastic nonwoven web does also affect the flexibility and elasticity of the three-layer laminate 19. Accordingly, a large bonded area will decrease the elasticity in the final laminate while sparsely distributed bonding points will have a very small or negligible influence on the elasticity.

After stretching of the activated first laminate 8, the film-side 14 of the laminate 8 is coated or sprayed with adhesive and is subsequently passed through a second bonding nip between two bonding rollers 16,17 together with a second, non-elastic nonwoven web 18. The adhesive is preferably a thermoplastic adhesive, although other types of adhesives may be used if so desired.

The resulting three-layer laminate 19 is elastically stretchable and has a selected elasticity primarily depending on the elasticity of the elastic film, the degree of tearing of the first nonwoven web in the incremental stretching step and the amount of stretching of the first laminate 8 before bonding to the second non-elastic nonwoven web 18. However, as set out above, the properties of the second non-elastic nonwoven web with regard to flexibility and extensibility and the amount of bonding effected in the second lamination step does also influence the elasticity of the final laminate.

The metal roll 4 in the first bonding nip is preferably an apertured suction roll so that three-dimensional forming and aperturing of the extruded elastic film 6 is achieved simultaneously with bonding of the film 6 to the first nonwoven web 1.

The second lamination step can, alternatively be carried out by thermal or ultrasonic bonding.

FIG. 1 is a highly schematic representation of the method according to an embodiment of the disclosure. However, all individual steps are well known and described in the art. Further, FIG. 1 does not show the widths of the individual webs. The laminate material can be made with all webs having the same width or CD extension. Alternatively, the second nonwoven web can have a greater width than the elastic film 6 and the first nonwoven web 1 and may extend past the first laminate on one or both sides thereof.

The three-layer laminate 19 shown in FIG. 2 comprises a first bi-laminate 8 consisting of a non-elastic fibrous nonwoven layer 1 and an elastic film. The elastic film is apertured and has a multiplicity of apertures arranged therethrough. The apertures may be three-dimensionally formed apertures as disclosed in WO 03/047488 or may be simple two-dimensional holes through the film. The laminate 19 further includes a second non-elastic nonwoven layer 18 that is bonded to the first laminate 8 by means of adhesive or by thermal bonding such as by application of heat or ultrasound.

The three-layer laminate 19 has a smooth face 21 on the side of the first nonwoven layer 1 and an irregular, puckered face 22 on the side of the second nonwoven layer 18. This is due to the second nonwoven layer 18 having been bonded to the first two-layer laminate 8 while the two-layer laminate was in an elastically extended state. The three-layer laminate 19 is soft, drapable, has a predetermined, selected elasticity and is exceptionally well suited for use in different kinds of disposable pant articles. The non-incrementally stretched second nonwoven layer provides reinforcement of the laminate, provides higher tensile strength perpendicularly to the direction of stretch, makes the laminate puncture resistant, and allows the laminate to be subjected to the pulling and stretching forces arising when putting on and taking off a pant article without breaking or tearing.

Moreover, by selecting nonwoven materials having thermoplastic properties, it is possible to obtain a laminate that can be readily incorporated in a disposable article by thermo-welding techniques. For example, in an article where the laminate is oriented with the first nonwoven layer 1 on the inside of the article, it may be beneficial if the first nonwoven layer is substantially or completely made of thermoplastic fibres, preferably polypropylene fibres. The first nonwoven layer can then be used to form side joins with good tensile strength. Conversely, if the laminate is oriented with the second nonwoven layer on the inside of the pant article, it may correspondingly be beneficial to choose a thermoplastic material for the second nonwoven layer. Since thermo-bonds used in side joins usually penetrate the welded materials, the orientation of the laminate with respect to the first and second nonwoven layers is normally not crucial for obtaining a thermobonded join as long as at least one of the layers is predominantly made of thermoplastic fibres or the combination of the two layers contain sufficient thermoplastic material in order to achieve sufficient bond strength.

Figure 4:
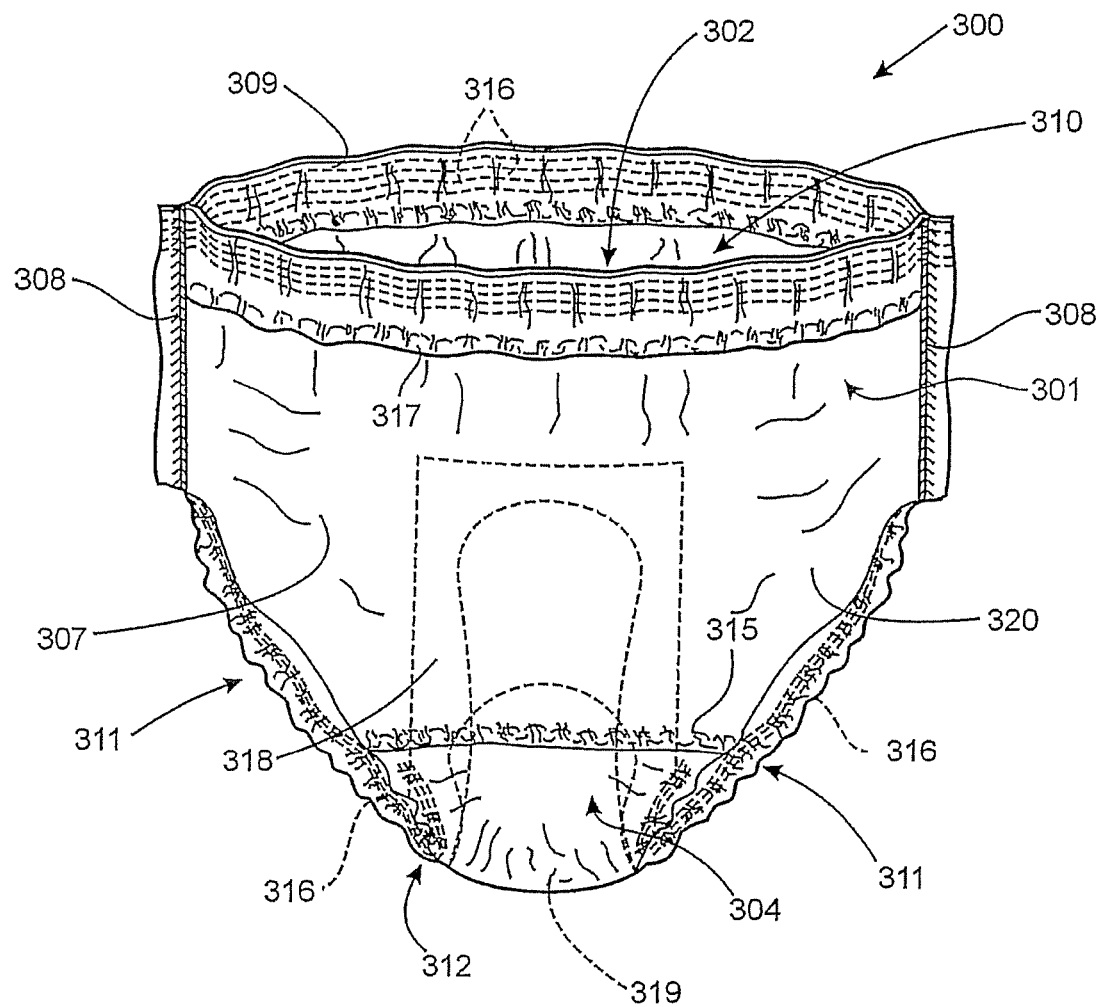
FIG. 4 shows the diaper in FIG. 3 with closed side joins.

The pant diaper 300 shown in FIGS. 3 and 4 is designed to enclose the lower part of a wearer's trunk like conventional underwear. In FIG. 3, the diaper is shown from the inside, i.e. from the side facing the wearer when the article is worn and in FIG. 4, the diaper is shown from the outside, or the garment-facing side, which is the side that is facing away from the wearer when the diaper is worn.

The diaper has a front panel 301, a back panel 302 and a crotch panel 303 extending between the front and back panels 301,302 and having a relatively narrow width as compared to the front and back panels 301,302. The front and back panels 301,302 are arranged to cover the wearer's hips and to extend over the belly and the back of the wearer to encircle the lower part of the wearer's trunk.

The diaper further comprises a core region 304 extending from the crotch panel 303 into the front panel 301 and the back panel 302. The front and back panels 301,302 form part of a chassis 307 that extends on the garment-facing side of the diaper 300 and covers and surrounds the core region 304. The chassis 307 comprises the front panel 301, the back panel 302 the crotch panel 303 and an elastic waist band 309 secured to the front and back panels. Each of the front and back panels has a waist edge, a crotch edge and a pair of side edges respectively.

Accordingly, the term "panel" is used herein to denote a functional part of the diaper chassis while the terms "region" and "portion" are used to denote the location of a particular feature of the diaper in the chassis or to describe the intended positioning of a particular part of the diaper in relation to a user's body. A panel may be a separate component or an integrated part of the chassis. A region or portion may have an extension fully or partially covering one or more panels.

The front and back panels are joined to each other along their side edges by thermobonding, ultrasonic welding, glue strings or the like to form side seams 308, as best shown in FIG. 4. The elastic waist band 309 consists of a front portion and a back portion, which are secured to the front panel 301 and the back panel 302, respectively. These portions of the waist band 309 are also joined to each other along the side seams 308. By joining the front and back panels 301, 302 and the waist band 309, the pant diaper 300 is provided with a waist opening 310 and a pair of leg openings 311.

FIG. 3 shows the diaper in a flat state with any elastic components that are attached to the chassis 307 under tensional stress drawn out to the full non-tensioned dimensions of the chassis 307. FIG. 4 shows the pant diaper 300 as it appears when the side seams 308 have been formed and the tensioned elastic elements have been allowed to relax and gather the chassis material to form elasticized leg and waist openings 311,310.

An elastic laminate 320 in accordance with the disclosure may cover the entire diaper between the front and back portions of the waist band 309, including the core region 304. However, it is preferred that a substantial part, i.e. at least 50% and preferably at least 75% of the crotch panel 303 of the pant diaper 300 is free from the elastic laminate material.

Hence, a crotch material 312 which preferably is a non-elastic material, such as a non-elastic nonwoven material, is arranged in the core region 304 of the article and overlaps with the elastic front and back panels 301,302. The crotch material 312 is joined along its transverse edges 313,314 to the front and back panels 301,302. In the shown embodiment, the crotch material 312 is joined by crotch seams 315 to the front and back panels 301,302 in an overlapping manner and forms the crotch panel 303. The joining can be made in any suitable way such as by ultrasonic welding, adhesively or similar. In alternative embodiments of the disclosure, an outer nonwoven material may extend continuously over the front and back panels 301, 302 and the crotch panel 303 so that no seams are needed between the panels 303,301,302.

In the shown example, the elastic waist band 309 comprises first and second plies of substantially non-elastic nonwoven material that is elasticized by one or more elongate elastic members 316, such as elastic threads or bands. The first and second plies can be formed from a single layer of material that has been folded over onto itself or can be two separate strips of material. The elastic members 16 are arranged in the waist band 309 in a tensioned state such that they contract and gather the nonwoven material in the waist band when they are allowed to relax, as shown in FIG. 4.

The elastic waist band 309 is secured to the front and back panels 301,302 with the elastic members 316 in an extended state and with the material in the front and back panels sandwiched between the nonwoven plies in the waist band. Alternatively, the elastic waist band can be a component that is prefabricated and joined to the outside or the inside of the front and back panels 301,302 respectively. The waist band join 317 between the waist band 309 and the front and back panels 301,302 can be made in any suitable way such as by means of ultrasonic welding, heat welding, or adhesively. A further option is to create the waist band 309 from one or more non-elastic nonwoven layers that are also parts of the front and back panels 301,302 and form continuous extensions thereof.

Elastic members 316 are also arranged at the edges of the leg openings 311 and serve to elasticize the leg openings. The elastic members at the leg openings can be any kind of conventional elastic elements such as elastic threads, bands, foam strips, or similar.

The planar extension of the core region 304 is defined by a liquid-impervious backsheet 318 arranged between an absorbent core 319 and the chassis 307. The liquid-impervious backsheet 318 has rectangular shape and the absorbent core is hour-glass shaped. Hence, the liquid-impervious backsheet 318 underlies the absorbent core 319 and the adjacent areas immediately outside the absorbent core 319. The nonwoven material in the crotch panel 303 is arranged on the garment-facing side of the liquid-impervious backsheet 318. The core region 304 extends into the front and back panels 301,302 so that the elastic laminate 320 in these panels overlap with the liquid-impervious backsheet 318 in the outer parts of the core region 304 as seen in FIG. 3. The elastic laminate 320 is arranged on the garment-facing side of the liquid-impervious backsheet 318.

As shown in the Figs., the elastic three-layer laminate 320 in accordance with an embodiment of the disclosure preferably forms the front and the back panels 301,302 of the pant diaper 300. However, it is possible to make only parts of the respective front and back panel 301,302 of the elastic three-layer laminate 320. In such embodiments, at least 20%, preferably at least 25%, more preferably at least 30% and most preferably at least 40% of the total surface area of the chassis as seen in the flat state shown in FIG. 3 is constituted by the elastic three-layer laminate in accordance with the disclosure. As an example, the elastic laminate may be used only in those parts of the front and back panels 301,302 that are intended to lie over the wearer's hips and thus form elastic side panels. It is also possible to design a pant article without any overlap between the core region 304 and the elastic laminate material in the front and back panels 301,302.

No additional elasticized side panels are needed when using the elastic laminate 320 in accordance with the disclosure. If desired, additional elasticized side panels may be provided, particularly in cases where the elastic laminate 320 is arranged only in parts of the front and/or back panels 301,302.

Description of Test Methods
Tensile strength (Reference: ASTM D 882)

The method measures tensile strength and elongation of different elastic materials. The tensile strength and elongation of a well-defined test piece is tested by means of a tensile tester.

Apparatus: Instron 4301
  Tensile tester connected to a computer
  Crosshead speed: 500 mm/min
  Clamp distance: 50 mm
  Sample preparation: Test samples are cut from the entire width of the material. The width of the sample shall be 25.4 mm and the length at least 50 mm longer than the clamp distance if possible. It is of importance that the edges of the sample are even and without break notches. The samples are conditioned for at least 4 h in 50% RH±5% RH and 23° C.±2° C. before testing.

Procedure: The tensile tester is calibrated according to the apparatus instructions and set to zero. The sample is mounted and it is ensured that it is not obliquely or unevenly fastened. The material is prevented from slipping by using clamps covered with galloon or similar material. The tensile tester is started, and stopped after the material has broken (if not automatically controlled). Measurements resulting from premature failure (i.e. the sample breaks at the clamp, or is damaged during preparation) are ignored, if possible.

The following results are expressed by the tensile tester/computer:
  Maximum force, N/25.4 mm
  Elongation at maximum force, %
  Break force, N/25.4 mm
  Elongation at break force, %
  Knee point, N/%

Elasticity Test

The method measures how an elastic material behaves at cycles of repeated load and unload. The sample is stretched to a predetermined elongation and a cyclic movement between 0 and said predetermined elongation is performed. Desired load and unload forces are recorded. The permanent, i.e. remaining, elongation of the relaxed material is measured.

A tensile tester, Lloyd LRX, able to perform cyclic movements and equipped with a printer/plotter or software presentation is used. The sample is prepared by cutting it to a width of 25 mm and a length that is preferably 20 mm longer than the distance between the clamps in the tensile tester.

The tensile tester is calibrated according to the apparatus instructions. The parameters needed for the test (load and unload forces) are adjusted to:

| | |
|---|---|
| Crosshead speed: | 500 mm/min |
| Clamp distance: | 50 mm |
| Preload: | 0.05 N |

The sample is placed in the clamps according to the marks and it is made sure that the sample I centred and fastened perpendicularly in the clamps. The tensile tester is started and three cycles between 0 and the predetermined elongation equal to the highest defined $1^{st}$ load are performed. Before the last cycle, the sample is relaxed for 1 minute, then the permanent elongation is measured by stretching the sample until a force of 0.1 N is detected and the elongation is read.

An elastic material is defined as a material having a permanent elongation after relaxation of less than 10% after the material has been subjected to an elongation of 30% in the test above. An elongation of 30% means an elongation to a length that is 30% longer than the initial length of the sample.

A non-elastic material as used herein is a material that has a permanent elongation after stretching and relaxation of more than 10% after having been subjected to an elongation of 30% as determined according to the elasticity test.

Puncture Strength

Puncture strength is measured according to ASTM Designation D3763-02. From penetration impact-type tests, this method produces data of load versus displacement. The maximum load for each sample is calculated.

EXAMPLES

The tensile strength in the machine direction (MD) and the cross direction (CD) was measured for three samples.

Sample A is a conventional activated three-layer laminate comprising an inner apertured three-layer elastomeric film of PE-SEBS-PE, basis weight 36 g/m² and two outer layers of spunbond material, PP (polypropylene), each having a basis weight of 22 g/m². The laminate was produced by applying one spunbond layer to the film while the film was in a tacky state and the other spunbond layer was adhesively laminated to the film layer using, for example, a pressure sensitive hot melt adhesive (glue amount 3 g/m²). The laminate was incrementally stretched, at which the non-elastic spunbond layers were stretched to a point below the elongation at maximum load to retain some strength in the spunbond layers.

The basis weights of the layers in the laminate are the basis weights after activation. Before activation, the basis weight of the individual layers was: inner film layer 40 g/m², outer spunbond layers 25 g/m² each and glue layer 3 g/m².

Sample B is a three-layer laminate comprising a first activated bi-laminate comprising a spunbond nonwoven PP layer having a basis weight of 22 g/m² and an apertured three-layer elastomeric film of PE-SEBS-PE, basis weight 36 g/m² that has been further laminated under stretching by 70% with a spunbond nonwoven layer having a basis weight of 18 g/m² (S1800PHW from Union Industries SpA).

Sample C is a three-layer laminate comprising the activated bi-laminate of Sample B that has been further laminated under stretching by 70% with a spunbond nonwoven layer having a basis weight of 20 g/m². (Lutrasil 9520×F from Freudenberg Fliesstoffe KG).

Sample D is a three-layer laminate comprising the activated bi-laminate of Sample B that has been further laminated under stretching by 25% with a creped nonwoven spunbond having a basis weight of 20 g/m². (From First Quality) The creped nonwoven was compacted to 50% at creping.

Sample E is the same three-layer laminate as in Sample D but with the bi-laminate stretched by 40% during lamination with the creped nonwoven layer.

The test results are shown in Table 1, below.

TABLE 1

| Sample | Tensile strength MD N/25 mm | Tensile strength CD N/25 mm | Puncture force N |
| --- | --- | --- | --- |
| A | 34 | 9 | 40 |
| B | 42 | 26 | 74 |
| C | 40 | 33 | 80 |
| D | 25 | 38 | 73 |
| E | 22 | 44 | 77 |

As can be seen in Table 1, the laminates B-E in accordance with embodiments of the disclosure have considerably higher MD and CD tensile strength and higher puncture resistance than the prior art three-layer laminate.

The invention should not be considered as limited by the above description; rather the scope and limitations of the invention are defined by the enclosed claims, and equivalents thereof.

The invention claimed is:

1. A method for producing an elastically stretchable laminate comprising at least three layers, comprising:
   a) Producing a first laminate comprising a first non-elastic fibrous nonwoven web and an elastic film;
   b) activating the first laminate by incremental stretching in at least one activation direction and partially tearing the first nonwoven web to render the first laminate elastically stretchable;
   c) stretching the activated first laminate to 10 to 200% in the activation direction; and
   d) laminating the stretched first laminate to a second non-elastic nonwoven web, such that the elastic film is between the first and the second nonwoven webs,
   wherein in the elastically stretchable laminate, the second non-elastic has a width greater than the width of the first laminate and extends past the first laminate on one or both longitudinal sides thereof, and
   wherein the activation direction is a longitudinal direction.

2. The method according to claim 1, wherein the first laminate is produced by extrusion coating of the first fibrous nonwoven web with the elastic film.

3. The method according to claim 1, wherein the elastic film is perforated.

4. The method according to claim 1, wherein the second non-elastic nonwoven web is adhesively bonded to the activated first laminate.

5. The method according to claim 1, wherein the second non-elastic nonwoven web is thermally or ultrasonically bonded to the activated first laminate.

6. The method according to claim 1, wherein the first laminate is stretched by 35-180% of its non-stretched extension.

7. The method according to claim 1, wherein the first and/or the second non-elastic fibrous nonwoven web comprises thermoplastic fibres.

8. The method according to claim 7, wherein the first and/or the second non-elastic fibrous nonwoven web comprises at least 50% thermoplastic fibres.

9. The method according to claim 1, wherein the second non-elastic nonwoven web is extensible.

10. The method according to claim 9, wherein the second nonelastic nonwoven web is a creped nonwoven.

11. An elastically stretchable three-layer laminate comprising a first non-elastic nonwoven web, a second non-elastic nonwoven web and an elastic film between the first and the second nonwoven webs wherein the first non-elastic nonwoven web and the elastic film form parts of a first elastic laminate that has been rendered elastic by incremental stretching in a longitudinal direction and partial tearing of the first nonwoven web,. and the first elastic laminate has been bonded to the second non-elastic nonwoven layer while in a stretched state, whereby the laminate is elastically stretchable, and wherein in the elastically stretchable laminate, the second non-elastic nonwoven web has a width greater than the width of the first laminate and extends past the first laminate on one or both longitudinal sides thereof.

12. The elastically stretchable laminate in accordance with claim 11, wherein the elastic film is perforated.

13. The elastically stretchable laminate in accordance with claim 11, wherein the first nonwoven web is a meltblown web or a spunbond web and the second nonwoven web is a meltblown web or a spunbond web.

14. The elastically stretchable laminate in accordance with claim 11, wherein the first nonwoven web has a basis weight of from 10-80 g/m$^2$.

15. The elastically stretchable laminate in accordance with claim 11, wherein the elastic film layer has basis weight of between 10 and 120 g/m$^2$.

16. The elastically stretchable laminate in accordance with claim 11, wherein the first and/or the second non-elastic nonwoven web comprises thermoplastic fibres.

17. The elastically stretchable laminate in accordance with claim 16, wherein the first and/or the second non-elastic fibrous nonwoven web comprises at least 50% thermoplastic fibres.

18. The elastically stretchable laminate in accordance with claim 11, wherein the second non-elastic nonwoven web is extensible.

19. The elastically stretchable laminate in accordance with claim 11, wherein the second non-elastic nonwoven web is a creped nonwoven.

20. The elastically stretchable laminate in accordance with claim 11, wherein the second non-elastic nonwoven layer in the laminate has not been stretched.

* * * * *